United States Patent
Campion et al.

(10) Patent No.: US 7,097,624 B2
(45) Date of Patent: Aug. 29, 2006

(54) MULTI-LAYER AND MULTI-SECTION COILS FOR GUIDE WIRE

(75) Inventors: Jon T. Campion, Crystal, MN (US); Todd D. Eungard, Maple Grove, MN (US); Pu Zhou, Eden Prairie, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 477 days.

(21) Appl. No.: 10/614,473

(22) Filed: Jul. 7, 2003

(65) Prior Publication Data

US 2004/0059258 A1    Mar. 25, 2004

Related U.S. Application Data

(63) Continuation of application No. 09/679,921, filed on Oct. 5, 2000, now abandoned.

(51) Int. Cl.
*A61B 5/00* (2006.01)
*A61M 25/00* (2006.01)

(52) U.S. Cl. ..................................... 600/585
(58) Field of Classification Search ................ 600/585; 604/523, 96.01
See application file for complete search history.

(56) References Cited

U.S. PATENT DOCUMENTS

| | | | |
|---|---|---|---|
| 3,973,556 A | 8/1976 | Fleischhacker et al. | 128/2 M |
| 4,003,369 A | 1/1977 | Heilman et al. | 128/2 M |
| 4,080,706 A | 3/1978 | Heilman et al. | 29/173 |
| 4,798,598 A | 1/1989 | Bonello et al. | 604/280 |
| 4,932,419 A | 6/1990 | de Toledo | 128/772 |
| 5,001,825 A | 3/1991 | Halpers | 29/456 |
| 5,107,852 A | 4/1992 | Davidson et al. | 128/772 |
| 5,253,653 A | 10/1993 | Daigle et al. | 128/772 |
| 5,345,945 A | 9/1994 | Hodgson et al. | 128/772 |
| 5,368,049 A | 11/1994 | Raman et al. | 128/772 |
| 5,373,856 A | 12/1994 | Grenouillet | 128/772 |
| 5,379,779 A | 1/1995 | Rowland et al. | 128/772 |
| 5,429,139 A | 7/1995 | Sauter | 128/772 |
| 5,433,200 A | 7/1995 | Fleischhacker, Jr. | 128/657 |
| 5,520,194 A | 5/1996 | Miyata et al. | 128/772 |
| 5,551,444 A | 9/1996 | Finlayson | 128/772 |
| 5,596,996 A | 1/1997 | Johanson et al. | 128/772 |
| 5,605,162 A | 2/1997 | Mirzaee et al. | 128/772 |
| 5,664,580 A | 9/1997 | Erickson et al. | 128/772 |
| 5,682,894 A | 11/1997 | Orr et al. | 128/654 |
| 5,706,826 A | 1/1998 | Schwager | 128/772 |
| 5,772,609 A * | 6/1998 | Nguyen et al. | 600/585 |
| 5,840,046 A | 11/1998 | Deem | 600/585 |
| 5,924,998 A | 7/1999 | Cornelius et al. | 600/585 |
| 5,951,494 A | 9/1999 | Wang et al. | 600/585 |
| 5,957,903 A | 9/1999 | Mirzaee et al. | 604/282 |
| 5,984,877 A | 11/1999 | Fleischhacker, Jr. | 600/585 |
| 6,004,279 A | 12/1999 | Crowley et al. | 600/585 |

(Continued)

*Primary Examiner*—Max F. Hindenburg
*Assistant Examiner*—Brian Szmal
(74) *Attorney, Agent, or Firm*—Crompton, Seager & Tufte LLC

(57) ABSTRACT

A guide wire having a coil disposed over the guide wire, wherein the coil is integrally formed of a single wire and has regions of differing properties over its length. Some wire embodiments have longitudinally alternating layer segments having differing properties including radiopacity, lubricity, hydrophilicity, hemo-compatibility, flexibility, malleability, stiffness, and shape memory properties. A coil may have numerous distinct property segments, while being formed from only a single wire and requiring only two points for affixation to the guide wire.

17 Claims, 3 Drawing Sheets

U.S. PATENT DOCUMENTS

| | | | |
|---|---|---|---|
| 6,019,736 A | 2/2000 | Avellanet et al. | 600/585 |
| 6,106,488 A | 8/2000 | Fleming et al. | 600/585 |
| 6,139,511 A * | 10/2000 | Huter et al. | 600/585 |
| 6,165,140 A * | 12/2000 | Ferrera | 600/585 |
| 6,306,105 B1 * | 10/2001 | Rooney et al. | 600/585 |
| 6,679,853 B1 * | 1/2004 | Jalisi | 600/585 |

* cited by examiner

MULTI-LAYER AND MULTI-SECTION COILS FOR GUIDE WIRE

This is a request for filing a continuation application, under 37 CFR §1.53(b), of pending prior application Ser. No. 09/679,921 filed on Oct. 5, 2000, now abandoned for an invention entitled MULTI-LAYER AND MULTI-SECTION COILS FOR GUIDE WIRE.

FIELD OF THE INVENTION

The present invention is related generally to medical devices. More specifically, the present invention is related to guide wires. The present invention includes intra-vascular guide wires.

BACKGROUND OF THE INVENTION

Guide wires are commonly used in minimally invasive procedures to guide catheters or other medical devices to a target site within the body. The guide wire can be advanced to the site, followed by advancing other medical devices such as guide catheters, therapeutic catheters, or diagnostic catheters, over the guide wire to the target site. Guide wires are commonly used in percutaneous transluminal coronary angioplasty (PTCA) procedures. In PTCA procedures, a guide wire can be inserted into the femoral artery of a patient near the groin, advanced over the aortic arch, further advanced into a coronary ostium, and thereafter into a coronary artery. A guide wire insertion procedure is typically performed under fluoroscopy, with the treating physician monitoring the guide wire distal end position within the patient. Examples of guide wires may be found in U.S. Pat. No. 3,973,556 to Fleischhacker et al.; U.S. Pat. No. 4,080,706 to Heilman et al.; U.S. Pat. No. 5,107,852 to Davidson et al.; U.S. Pat. No. 5,253,653 to Daigle et al.; U.S. Pat. No. 5,345,945 to Hodgson et al.; and U.S. Pat. No. 5,368,049 to Raman et al.

One guide wire type has a distal region which is sufficiently flexible and has a small enough outside diameter to pass into successively smaller and more tortuous coronary vessels. The desired mechanical properties of the guide wire are often met with fabrication from stainless steel or Nitinol, which are largely invisible under fluoroscopy. The small diameter, flexible distal regions are thus difficult to monitor under fluoroscopy, without added radiopacity. Such radiopacity is often provided with radiopaque distal coils.

Guide wires currently have a coil or coils disposed in the distal region, for example, in the distal-most foot of the catheter. A coil is typically formed of a wire wound into a coil and disposed about a guide wire core or shaft. The coil is often wound to meet a close outside diameter dimension specification having a tight tolerance. Single coils often serve as a radiopaque marker. Coils can be made out of radiopaque metal wire, or metal wire that is plated with a more radiopaque metal. The radiopaque coils can be further coated to provide a more lubricous or hemo-compatible surface.

Some guide wires have more than one coil, or a coil formed from more than one segment. In one example, a distal portion of a guide wire has a series of coils disposed over the distal-most foot of the guide wire, to provide a series of markers to allow for taking measurements under fluoroscopy. A series of radiopaque coils, spaced about one centimeter apart, can effectively provide a ruler which is radioscopically visible, and can be used by the treating physician to measure distances within the heart. It may also be desirable to provide coils having different surface properties over the length of the guide wire. For example, it may be desirable to provide more lubricious distal coils and less lubricious proximal coils.

In guide wires having more than one coil, the coils may be affixed to the core wire at each end of each coil. Thus, a guide wire distal portion having four separate affixed coils may require eight welds joining the coil ends to the core wire. What would be desirable are guide wires having multiple coils having varying properties, while requiring the formation, and affixing to core wire, of only a single coil.

SUMMARY OF THE INVENTION

The present invention provides methods for making a guide wire portion having a coil disposed about a core wire. The methods include providing a guide wire and providing a wire to be used in forming the coil. A first property can be generated over a first portion or portions of the wire and a second property can be generated over a second portion or portions of the wire, where the first and second properties are different from each other. The wire can then be formed into a coil, and the coil secured to a guide wire. Some embodiments have only one section having a first property and another section having a second property, while other embodiments have multiple, alternating sections having first and second properties. First and second properties to be imparted to the wire can include radiopacity, lubricity, hydrophilicity, hemo-compatibility, flexibility, malleability, stiffness, and shape memory.

In one embodiment, longitudinally alternating layer segments of highly radiopaque and less radiopaque materials are alternated to provide a radiopaque series of markers for use under fluoroscopy. In one method, a highly radiopaque material is plated or otherwise bonded to the core wire. In this embodiment, alternating regions are created which do not have the highly radiopaque material plated or bonded to the core wire. In one embodiment, the high radiopacity is imparted by plating a core wire with a radiopaque material, for example, gold or tungsten. In another embodiment, high radiopacity is imparted by extruding or otherwise coating a core wire with a polymeric material being highly loaded with a radiopaque filler such as tungsten, bismuth, barium, barium sulfate, platinum, or tungsten.

One wire according to the present invention has longitudinally alternating layer segments formed over a core wire, and a more outer layer formed over the longitudinally alternating layer segments. In one example, a metallic core wire has alternating regions of radiopaque plating thereover, as well as a continuous length of a lubricious hydrophilic coating disposed over the wire length over both radiopaque and radiotranslucent regions. In yet another embodiment, a tie-layer is disposed between the central core wire and the outer layer. In one embodiment, a tie-layer serves as a polymer substrate to bind an outer polymer layer to the inner metallic core wire, where the inner metallic core wire may not as readily bind the outer polymeric layer. In another embodiment, an intermediate tie-layer is disposed between a more outer layer and a more inner layer coating the core wire.

In one set of methods, a core wire is treated in alternating regions to impart alternating properties to the core wire. In one embodiment, alternating regions are treated to inhibit binding of a subsequently applied material, while in other embodiments, alternating regions are treated to enhance binding of a subsequently applied material. In one embodiment, a core wire is exposed to ionizing radiation, to form polymeric initiation sites on the wire surface. Subsequent exposure of the core wire to monomer can result in polymerization primarily at the previously ionized sections. In another embodiment, the alternating treated regions receive application of a release agent. In this embodiment, subsequent application of a material such as a polymer will initially result in a continuous coating of polymer over both the release agent treated regions and the non-release agent treated regions. In a subsequent removal step, the regions previously treated with release agent can have the outer layer removed, while the non-treated regions can retain the outer layer.

Treated wire thus formed according to the present invention can be wound about a mandrel and the finished coil disposed over a guide wire and secured to the guide wire. In a preferred embodiment, the coil is secured to the guide wire in a proximal location and a distal location. In one embodiment, the wire thus formed may be wound into a coil in place around the guide wire. The formed coil may be affixed to the guide wire using methods well known to those skilled in the art. In one embodiment, the coil is formed as a single, tightly wound coil segment having substantially equal spacings between coil strands. In yet another embodiment, the formed coil has alternating tightly wound and loosely wound segments. The coil formed by the present invention can thus be made from an integrally formed wire having various properties over its length. The integrally formed coil may have alternating properties over its length while requiring only two affixation points for securing the coil to the guide wire.

DETAILED DESCRIPTION OF THE PREFERRED EMBODIMENTS

Figure 1:
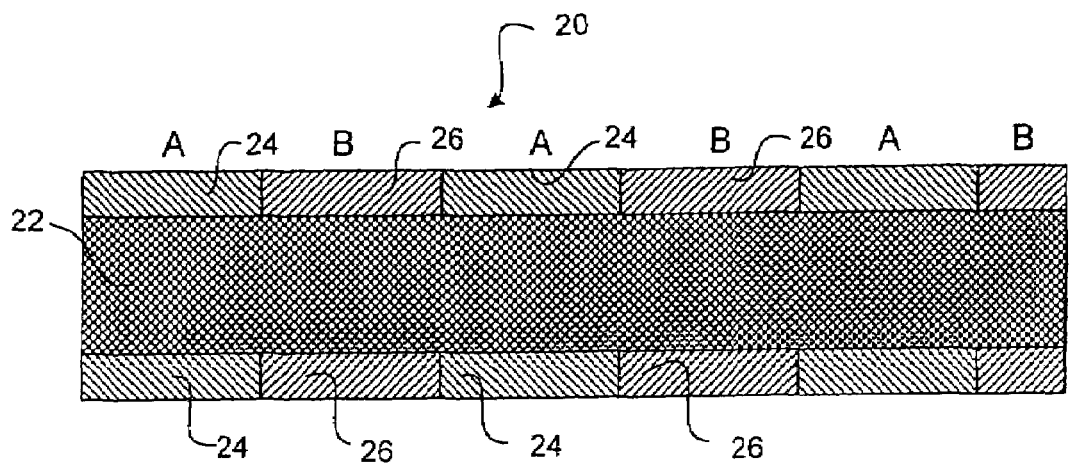
FIG. 1 is a fragmentary, transverse, cross-sectional view of a wire for use in a guide wire coil, the wire having longitudinally alternating layer segments with different properties.

FIG. 1 illustrates a transverse, cross-sectional view through a length of wire 20, which can be used to form a guide wire coil. Wire 20 can include a central core wire 22 having alternating first layer segments 24 and second layer segments 26. First segments 24 are denoted by "A" and have a first property. Second segments 26 are denoted by "B", and have a property different from that of first segments 24. The alternating properties can include properties such as radiopacity, lubricity, hydrophilicity, hemo-compatibility, flexibility, malleability, stiffness, and shape memory characteristics.

In one embodiment, alternating layer segments 24 and 26 represent alternating sleeves disposed over central core wire 22. In another embodiment, alternating layer segments 24 and 26 represent alternating sections of coating over core wire 22. In yet another embodiment, alternating layer segments 24 and 26 represent the presence and absence, respectively, of a layer disposed over central core wire 22. In one embodiment, layer 24 represents a PTFE layer, and layer 26 represents a metallic or other radiopaque material deposited where the PTFE has been stripped away, with the radiopaque material plated or otherwise bonded to core wire 22. In one embodiment, alternating layer segments 24 and 26 represent alternating layer segments having varying radiopacity therebetween. In another embodiment, layer segments 24 have a high radiopacity, and layer segments 26 have a lower radiopacity than layer segments 24. In yet another embodiment, the difference in radiopacity is imparted by plating layer segments 24 with a highly radiopaque substance such as gold or platinum, while not plating layer segments 26. In another embodiment, the differing radiopacity is imparted by coating layer segments 24 with polymeric material highly loaded with a radiopaque material such as tungsten, platinum, bismuth, barium sulfate, or barium. In embodiments having highly radiopaque loaded polymer, layer segments 26 can represent either a lack of polymer or polymer not being as highly radiopaquely loaded as layer segments 24.

In some embodiments, alternating layer segments 24 and 26 have varying lubricity. In one embodiment, wire 20 has only two sections, with one section being more lubricious than the other section. This may be of particular importance, where a distal coil segment is to be either more or less lubricious than a proximal coil segment. The varying lubricity may be imparted by forming layer segments 24 and 26 of different materials, or treating layer segments 24 and 26 with different processes.

In one embodiment, alternating layer segments 24 and 26 have differing hydrophilic properties therebetween. In another embodiment, the hemo-compatibility of the coil may be varied over the length of the coil by forming first layer 24 of a material having first hemo-compatibility properties and forming second layer 26 of a material having second hemo-compatibility properties.

In one embodiment, the flexibility of the coil is varied with distal to proximal location by varying the properties of the wire which make up the coil. In another embodiment, the flexibility, malleability, stiffness, and/or shape memory properties are varied over layer segments 24 and 26. In yet another embodiment, the coil thus formed has a distal section which is easier to bend and/or retains an imparted bend more readily than a more proximal coil section. This may be desirable, where the treating physician wishes to impart a hook or bend to the distal coil, but wishes the more proximal coil segment to remain unchanged. A wire segment may be made easier to bend relative to the other segments by heat treating selected segments or forming a more rigid sleeve over the other segments. A wire segment may have shape memory properties imprinted by selective treating or by forming a sleeve or layer of shape memory material over the segments.

Figure 2:
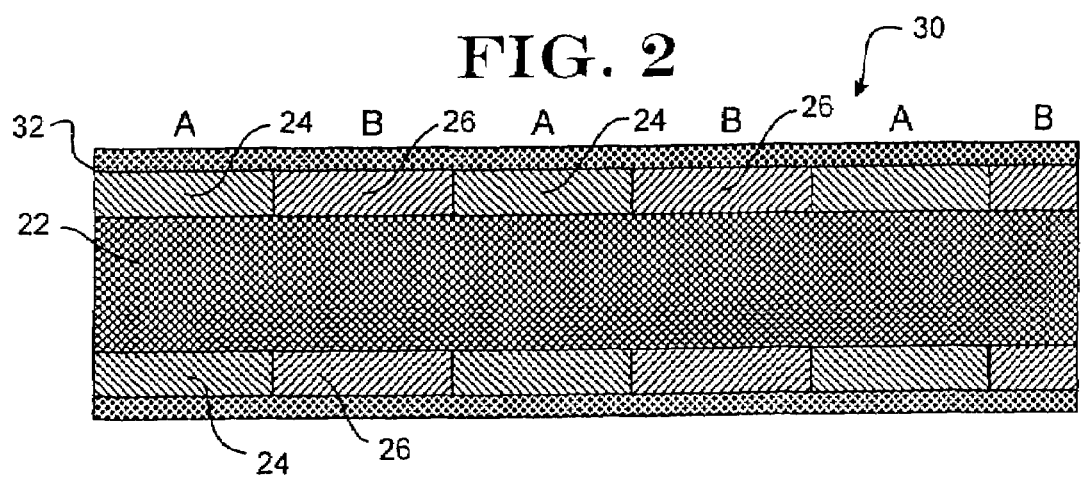
FIG. 2 is a fragmentary, transverse, longitudinal cross-sectional view of a wire similar to that of FIG. 1, having a coating or sleeve over the alternating layer segments.

FIG. 2 illustrates a wire 30 similar to wire 20 of FIG. 1, further having a layer 32 disposed over wire 20. Layer 32 can include a polymeric coating or sleeve disposed over the alternating layer segments 24 and 26. In some embodiments, layer 32 includes a radiopaque material, while in other embodiments, layer 32 serves no radiopaque function. Outer layer 32 can be useful to provide a more lubricious or more hemo-compatible surface over alternating radiopaque and non-radiopaque layers. Outer layer 32 may include polymers such as lubricious polymers such as polyvinylpyrrolidone (PVP).

Figure 3:
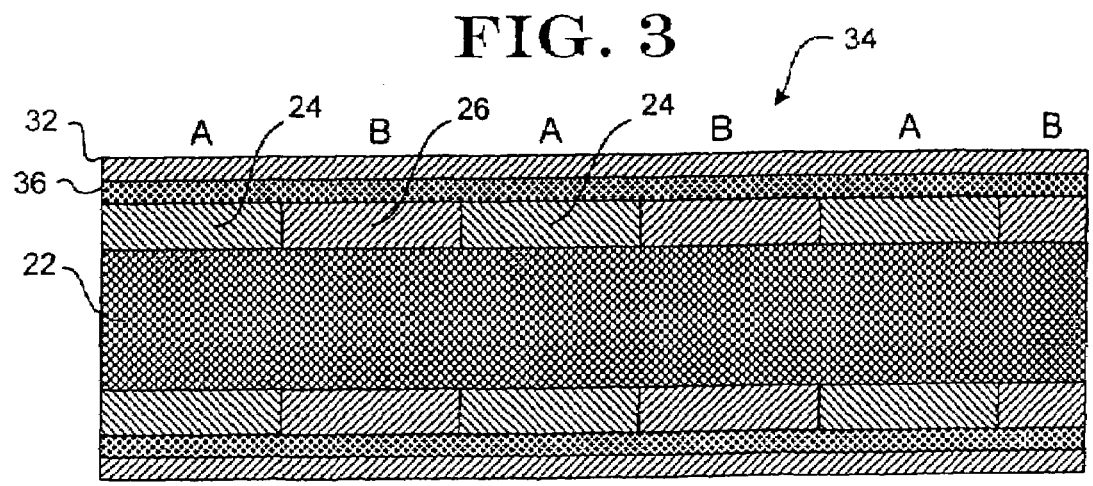
FIG. 3 is a fragmentary, transverse, cross-sectional view of a wire similar to that of FIG. 2, having an intermediate tie-layer disposed between the alternating layer segments and the coating.

FIG. 3 illustrates another wire 34 having a wire portion represented by wire 20 of FIG. 1, having outer layer 32 of FIG. 2, and also having an intermediate or tie-layer 36 disposed between layer 32 and layer segments 24 and 26. In one embodiment, intermediate or tie-layer 36 can serve to bind outer layer 32 to more inner layer segments 24 and 26, where outer layer 32 and layer segments 24 or 26 are not readily bound together. Intermediate layer 36 may also represent a coating or treatment upon the outer surface of layer segments 24 and 26 which imparts improved binding properties with respect to outer layer 32. In another embodiment, not requiring illustration, tie-layer 32 can be disposed between core wire 22 and layer segments 24 and 26. In one embodiment, intermediate layer 36 serves as a polymer substrate and can be formed of materials such as lubricious polymers such as polyvinylpyrrolidone (PVP).

Figure 4:
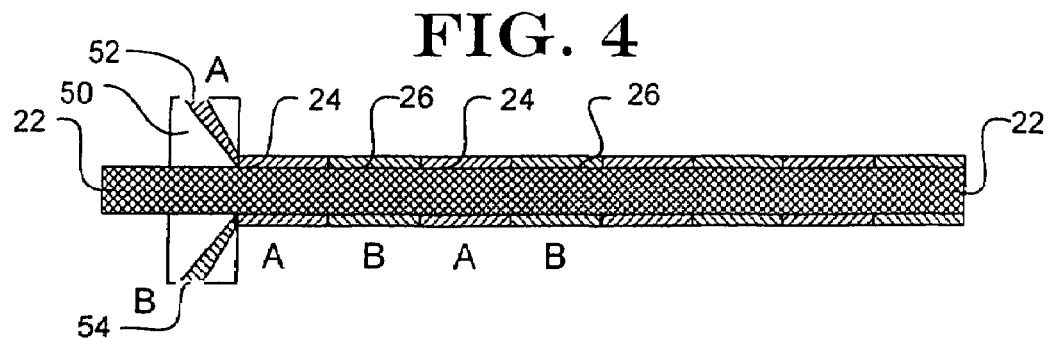
FIG. 4 is a highly diagrammatic, transverse, cross-sectional view of an extrusion head coating a core wire with longitudinally alternating layer segments having different properties.

FIG. 4 represents a system including an extrusion head 50 for coating core wire 22 with alternating layer segments of material. Extrusion head 50 can include channels within for receiving and applying more than one material. In the embodiment illustrated in FIG. 4, extrusion head 50 has a first channel 52 for accepting a first material "A" and a second channel 54 for accepting a second material "B". As shown in FIG. 1, core wire 22 enters extrusion head 50, and has longitudinally alternating layer segments 26 and 24 applied thereover. In some embodiments, alternating layers 26 and 24 represent alternating layer segments having material in layer segments 26, and no material in layer segments 24. In one embodiment, an extrusion head can be employed which coats core wire 22 with only a single layer such as layer segments 26. In this embodiment, layer segments 26 can be removed in alternating regions by being stripped from wire 22, leaving wire 22 exposed. The exposed layer segments 24 can then be treated to vary the properties relative to layer segments 26. In one embodiment, the exposed sections of core wire 22 are plated with a radiopaque material such as gold or tungsten.

Figure 5:
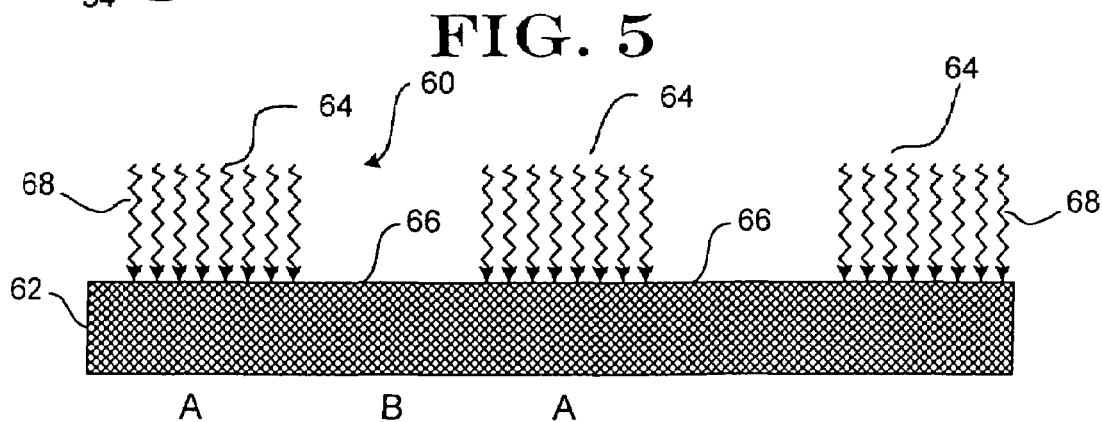
FIG. 5 is a highly diagrammatic, transverse, cross-sectional view of a core wire receiving treatment in longitudinally alternating layer segments.

FIG. 5 illustrates a method for forming longitudinally alternating layer segments over a core wire 62 to form a section of a wire 60. Wire 60 can be made by treating core wire 62 in alternating regions 64, but not treating core wire 62 in regions 66. The alternating regions of treatment are indicated by arrows 68. Core wire 62 can represent a bare, metallic wire, for example, core wire 22 of FIG. 1. Core wire 62 can also represent a bare wire such as core wire 22 of FIG. 1, which has been further coated with another material.

Treatment region 64 can include exposure to ionizing radiation to form polymerization initiation sites on core wire 62. In this embodiment, treatment region 64 will have polymerization initiation sites on the wire surface, which can initiate polymerization in a subsequent step of exposing the core wire to monomer. In one embodiment, treatment regions 64 correspond to the application of an agent to inhibit adhesion or bonding of a subsequently applied material such as a polymer. In another embodiment, treatment region 64 represents the application of an agent applied to enhance adhesion or bonding of a subsequently applied material. Treatment region 64 may thus correspond to the application of a tie-layer or to the application of a release agent.

Figure 6:
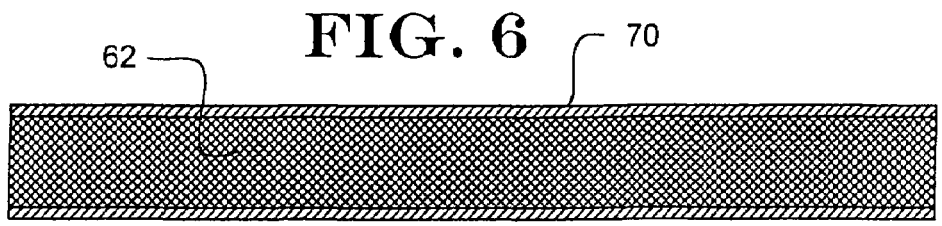
FIG. 6 is a highly diagrammatic, transverse cross-sectional view of the wire of FIG. 5, after a layer has been formed over the treated layer segments of FIG. 5.
Figure 7:
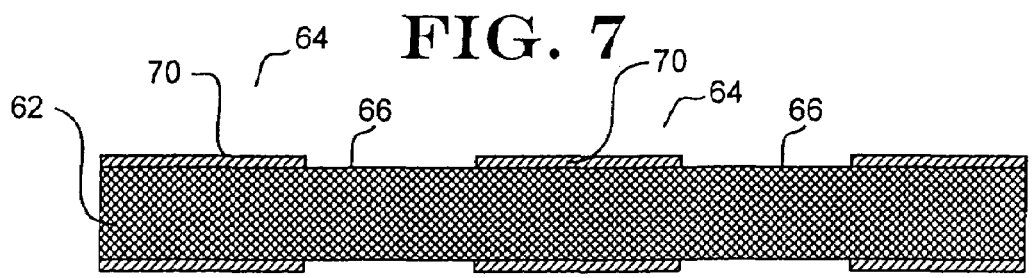
FIG. 7 is a highly diagrammatic, transverse, cross-sectional view of the wire of FIG. 6, after untreated coating regions of the layer applied in FIG. 6 have been removed.
Figure 8:
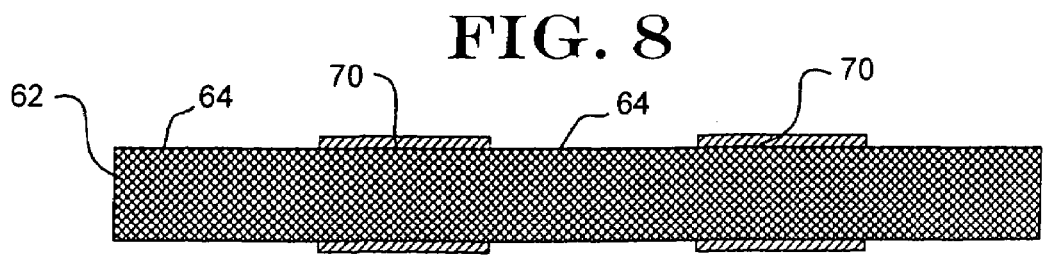
FIG. 8 is a fragmentary, transverse, cross-sectional view of the wire of FIG. 6, after treated coating regions of the layer applied in FIG. 6 have been removed.

FIG. 6 illustrates treated wire 60 of FIG. 5, after further processing to expose treated wire 60 to another material, to form a layer over wire 62. FIG. 6 illustrates a layer 70 formed over wire 62 of FIG. 5. FIG. 7 illustrates the wire of FIG. 6, after subsequent processing to remove portions of layer 70. In particular, FIG. 7 illustrates an embodiment where treatment regions 64 of FIG. 5 enhanced bonding between layer 70 and core wire 62. In one embodiment, the subsequent removal processing represented by FIG. 7 may include washing to remove loosely bound portions of layer 70 from core wire 62. FIG. 8 illustrates an embodiment where treatment regions 64 of FIG. 5 acted to inhibit binding between layer 70 and central wire 62. In one example, treatment regions 64 represent the application of a release agent to the central core wire. FIG. 8 then represents the removal of layer 70 from regions pretreated in treated regions 64.

Figure 9:
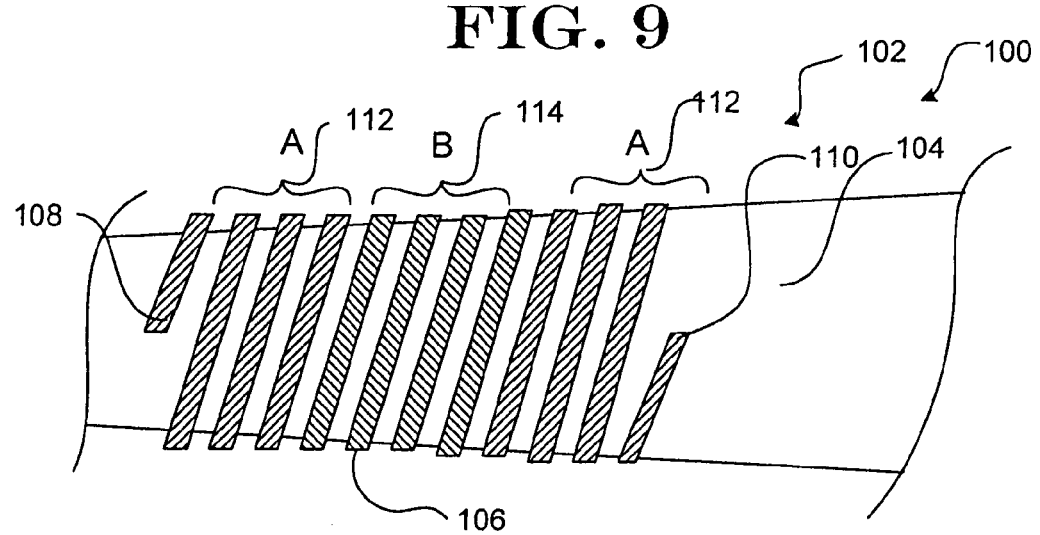
FIG. 9 is a fragmentary, highly-diagrammatic side view of a guide wire distal portion having a coil with alternating regions having different properties.

FIG. 9 illustrates a guide wire 100, having a distal portion 102, including a coil 106 secured at a distal location 108 and at a proximal location 110, being secured to a core wire 104. Coil 106 includes a plurality of alternating first property regions 112, and alternating second property regions 114. Alternating regions 112 and 114 may be formed by methods previously discussed, for example, with respect to FIGS. 1–4. The wire produced by steps such as those illustrated in FIGS. 1–4 can be wound into a coil, either in place, on a coil wire 104, or externally about a mandrel, and then moved into position over core wire 104. In one embodiment, there are only two varying property regions in coil 102. In another embodiment, coil 102 has alternating regions of radiopacity, and the coil can serve as a radiopaque marker.

Figure 10:
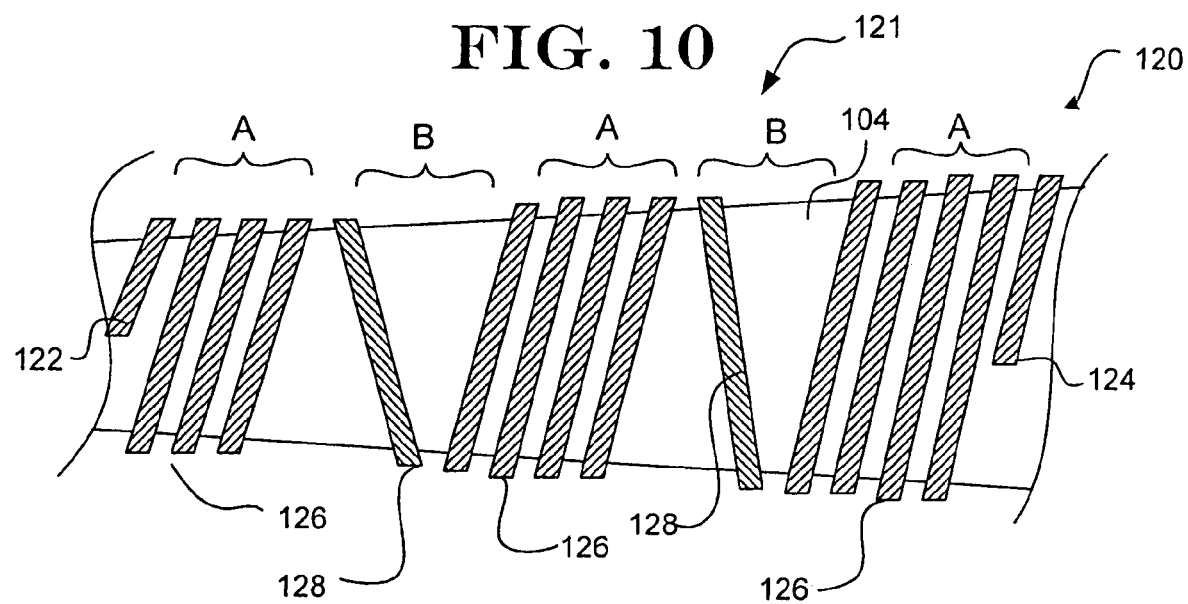
FIG. 10 is a fragmentary, highly-diagrammatic side view of a guide wire having a distal coil formed of alternating, tightly wound segments connected by sparse segments therebetween.

FIG. 10 illustrates another guide wire 120, having a coil 121 disposed thereover, affixed to core wire 104 at a distal location 122, and at a more proximal location 124. Coil 122 includes alternating first property regions 126 and second property regions 128. In the embodiment illustrated, first regions 126 are tightly wound coil segments, while second segments 128 are more sparsely wound, and have a helix pitch longer relative to that of first region 126. Second region 128 can provide a less radiopaque region under fluoroscopy. FIG. 10 illustrates how coil segments separated therebetween by relatively long distances can be secured to a guide wire by securing only a small number of guide wire coil locations, for example, two locations in FIG. 10. The design illustrated by FIG. 10 can be of use where the coil property is to be varied over a relative long length of guide wire. In one embodiment, coil section 126 of FIG. 10 may be more malleable, or retain shape memory more readily, than the more proximal coil regions. In this embodiment, regions 126 may be more easily bent into a curve by a treating physician, relative to more proximal regions. In use, the more malleable and/or shape retaining distal portions can thus have shape changes imparted to a single coil by treating the wire forming the distal portion of the coil differently than the wire forming the proximal section of the coil. FIG. 10 also illustrates a method for alternating radiopacity by both alternating the treatment regimes for the wire forming the coil, and also by separating tightly wound coil segments by more sparsely wound coil segments.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A guide wire comprising:
    an elongate wire including a core having an outer surface having an area per unit length, a tubular first layer disposed about the core having an inner surface having an area per unit length of no more than the area per unit length of the outer surface of the core, wherein a portion of the layer has a topology selected from the topology of a single-lumen tube or the topology of a single-lumen tube having a slit;
    wherein the elongate wire has a first property over a first portion and a second property over a second portion, wherein the first property is different from the second property, and wherein the elongate wire is formed into a coil; and
    wherein the elongate wire forming the coil comprises a continuous wire.

2. The guide wire of claim 1, wherein said first and second properties are selected from the group consisting of radiopacity, lubricity, hydrophilicity, hemocompatibility, flexibility, malleability, stiffness, and shape memory.

3. The guide wire of claim 1, wherein at least some of said first property is provided by the layer.

4. The guide wire of claim 1, wherein the layer is a sleeve.

5. The guide wire of claim 4, wherein the sleeve is polymeric.

6. The guide wire of claim 1, wherein the layer is a material coating.

7. The guide wire of claim 6, wherein the coating comprises a different material than the core.

8. The guide wire of claim 1, wherein the elongate wire further comprises a second layer disposed on a portion of the core free from the first layer.

9. The guide wire of claim 8, wherein the first layer and the second layer alternate.

10. The guide wire of claim 1, wherein the first layer is disposed on noncontiguous portions of the core.

11. A guide wire as in claim 1, wherein the first and second properties differ in radiopacity from each other.

12. A guide wire as in claim 1, wherein the coil is helically disposed about a guide wire distal portion.

13. A guide wire as in claim 1, wherein the pitch of the coil at a first section is different than the pitch of the coil at a second section.

14. A guidewire having a distal end portion provided with radiation impermeability and flexibility, the guidewire comprising:
    a core wire having a distal end portion and a proximal end portion and a circular cross-section decreasing in diameter at the distal end portion toward a distal end of the core wire, and
    a coil wire having a constant diameter provided coaxially with the core wire and provided on the distal end portion of the core wire, the coil wire comprising a continuous wire including a plurality of alternating regions of radiopacity.

15. A guide wire comprising:
    an elongate wire including a core having an outer surface having an area per unit length, a polymeric tubular sleeve disposed about the core having an inner surface having an area per unit length of no more than the area per unit length of the outer surface of the core, wherein a portion of the sleeve has a topology selected from the topology of a single-lumen tube or the topology of a single-lumen tube having a slit; and
    wherein the elongate wire has a first property over a first portion and a second property over a second portion, wherein the first property is different from the second property, and wherein the elongate wire is formed into a coil.

16. A guide wire comprising:
    an elongate wire including a core having an outer surface having an area per unit length, a tubular first layer disposed about the core having an inner surface having an area per unit length of no more than the area per unit length of the outer surface of the core, wherein a portion of the layer has a topology selected from the topology of a single-lumen tube or the topology of a single-lumen tube having a slit;
    the elongate wire further including a second layer disposed on a portion of the core free from the first layer; and
    wherein the elongate wire has a first property over a first portion and a second property over a second portion, wherein the first property is different from the second property, and wherein the elongate wire is formed into a coil.

17. A guide wire comprising:
    an elongate wire including a core having an outer surface having an area per unit length, a tubular first layer disposed about the core having an inner surface having an area per unit length of no more than the area per unit length of the outer surface of the core, wherein a portion of the layer has a topology selected from the topology of a single-lumen tube or the topology of a single-lumen tube having a slit;
    the elongate wire further including a second layer disposed on a portion of the core free from the first layer, and wherein the first layer and second layer alternate; and
    wherein the elongate wire has a first property over a first portion and a second property over a second portion, wherein the first property is different from the second property, and wherein the elongate wire is formed into a coil.

* * * * *